(12) United States Patent
Gobet

(10) Patent No.: US 11,534,345 B2
(45) Date of Patent: Dec. 27, 2022

(54) DEVICE FOR SELECTING AN EVC ORTHOSIS

(71) Applicant: LABORATOIRES INNOTHERA, Arcueil (FR)

(72) Inventor: Arnaud Gobet, Paris (FR)

(73) Assignee: LABORATOIRES INNOTHERA, Arcueil (FR)

( * ) Notice: Subject to any disclaimer, the term of this patent is extended or adjusted under 35 U.S.C. 154(b) by 345 days.

(21) Appl. No.: 16/809,843

(22) Filed: Mar. 5, 2020

(65) Prior Publication Data
US 2020/0289333 A1 Sep. 17, 2020

(30) Foreign Application Priority Data

Mar. 11, 2019 (FR) ...................................... 19 02442

(51) Int. Cl.
*A61F 13/08* (2006.01)
*G01J 3/02* (2006.01)
(Continued)

(52) U.S. Cl.
CPC ............ *A61F 13/08* (2013.01); *G01J 3/0264* (2013.01); *G01J 3/462* (2013.01); *G01J 3/463* (2013.01); *G01J 3/524* (2013.01)

(58) Field of Classification Search
CPC ... A61F 13/08; G01J 3/463; G01J 3/46; G01J 3/52

See application file for complete search history.

(56) References Cited

U.S. PATENT DOCUMENTS

2007/0058858 A1* 3/2007 Harville ................ G06Q 30/02
382/165
2011/0064307 A1 3/2011 Kalla et al.
(Continued)

FOREIGN PATENT DOCUMENTS

EP  1297785 A1 *  4/2003  ........... A45D 44/005
EP  1486901 A2 * 12/2004  ................ G01J 3/50
(Continued)

OTHER PUBLICATIONS

French Search Report for Corresponding French Application No. 1902442, dated Feb. 10, 2020, 2 pages.
(Continued)

*Primary Examiner* — Maurice C Smith
(74) *Attorney, Agent, or Firm* — Ronald M. Kachmarik; Cooper Legal Group LLC

(57) ABSTRACT

Method for selecting an elastic venous restraint orthosis intended to be slipped onto a lower limb of a patient. Acquisition of a photograph representing the skin of the limb and a calibration map including one or more calibration zones. The calibration map is placed on the limb in a position termed the "acquisition position." Calibration of the photograph by the calibration zone or zones, in such a way that the representation of the skin on the photograph exhibits a calibrated colour. Selection, as a function of the calibrated colour, by computer and from a set of colours of a tone chart, of a tone chart colour, preferably of the tone chart colour closest to the calibrated colour, termed the "optimal colour," and then determination, by computer, of an orthosis colour as a function of the tone chart colour selected. Selection of an orthosis exhibiting the orthosis colour.

12 Claims, 1 Drawing Sheet

(51) Int. Cl.
*G01J 3/46* (2006.01)
*G01J 3/52* (2006.01)

(56) References Cited

U.S. PATENT DOCUMENTS

| | | |
|---|---|---|
| 2013/0057866 A1 | 3/2013 | Hillebrand et al. |
| 2014/0372954 A1* | 12/2014 | Smith .................. A61F 2/5046 29/527.1 |
| 2018/0146175 A1 | 5/2018 | Mui |

FOREIGN PATENT DOCUMENTS

| | | | |
|---|---|---|---|
| WO | 2007/011929 A2 | 1/2007 | |
| WO | WO-2007011929 A2 * | 1/2007 | ................ G01J 3/02 |
| WO | 2012/038474 A1 | 3/2012 | |
| WO | WO-2012123693 A1 * | 9/2012 | ......... G05B 19/4099 |

OTHER PUBLICATIONS

Applegate, et al., "Color Standardization for Laminated Plastic Prosthetic Components", Oct. 1, 1973, XP055665503, extract from the internet, http://www.oandplibrary.org/op/pdf/1973_03_027.pdf.

* cited by examiner

DEVICE FOR SELECTING AN EVC ORTHOSIS

TECHNICAL FIELD

The present invention relates to a method for selecting an elastic venous compression, or EVC, orthosis, hereinafter "orthosis", indicated in case of venous insufficiency of a lower limb of a patient. The invention also relates to a selection device that can be implemented in a method according to the invention.

PRIOR ART

Elastic venous compression orthoses, formerly known as "restraint stockings (or socks)" or "restraint tights", are textile medical devices producing a therapeutic effect by compression of the lower limbs, as opposed to "hold-up stockings" (or else "support stockings" or "anti-fatigue stockings") and to "fashion stockings", which are not medical devices for therapeutic purposes.

Elastic venous compression orthoses are designed to produce a therapeutic effect by compression of the lower limb over a greater or smaller extent, customarily with an upwards degressive compression profile starting from the ankle.

The effectiveness of a treatment by means of an orthosis is directly related to the patient's compliance with the medical prescription. Through lack of proper observance, the disease can worsen, thereby giving rise to an additional risk for the patient, and also to costs for Social Security or care financing organizations.

Therefore, a permanent need exists for solutions making it possible to improve observance.

An aim of the invention is to meet this need, at least partially.

Moreover, a device which associates a mobile telephone and a calibration map is known from WO 2007/011929. This device is intended to facilitate the search for decorative objects, for example a piece of furniture, in a colour coordinated with that of items that the users have at home, for example a wallpaper. This document does not describe, or suggest, that such a device can be used in the medical field, and more particularly to improve the observance of a treatment.

DISCLOSURE OF THE INVENTION

Summary of the Invention

The invention proposes a method for selecting an EVC orthosis intended to be slipped onto a lower limb of a patient, the said method comprising the following steps:
1) acquisition of a photograph representing the skin of the said limb and a calibration map comprising one or more calibration zones, the calibration map being placed on the said limb in a position termed the "acquisition position";
2) calibration of the photograph by means of the calibration zone or zones, in such a way that the representation of the said skin on the photograph exhibits a calibrated colour, and then selection, as a function of the calibrated colour, by computer and from a set of colours of a tone chart, of a tone chart colour, preferably of the tone chart colour closest to the calibrated colour, termed the "optimal colour", and then determination, by computer, of an orthosis colour as a function of the tone chart colour selected;
3) selection of an orthosis exhibiting the said orthosis colour.

As will be seen in greater detail in the subsequent description, the inventor has noted that, until the present invention, the patient passed their hand inside the orthosis to stretch it and thus get an idea of its appearance in the slipped-on position. However, this method of selection led to disappointments. The inventor has indeed noted that this method does not allow precise simulation, in particular on account of the fact that the colour of the hand is not always the same as that of a lower limb and that the tension applied varies greatly as a function of the size of the patient's hand. This problem is all the more critical the more strongly elastic the orthosis and therefore liable to change appearance appreciably when it is slipped on.

A method according to the invention advantageously makes it possible to select an orthosis rapidly, in an objective manner and without having to slip it on. It advantageously limits the risk of disappointment. Observance is thereby improved. Preferably, the orthosis colour determined in step 2), termed the "derived colour", is different from the orthosis colour closest to the tone chart colour selected. The derived colour makes it possible to take account of subjective effects which are difficult to anticipate and which lead to the said optimal colour not being chosen.

A method according to the invention can further comprise one or more of the following optional characteristics:
- the derived colour is determined by statistical analysis of responses of a group of patients to an opinion survey;
- the group of patients consists of people for whom the implementation of steps 1) and 2) culminates, on average, in the said selected tone chart colour;
- the group of patients consists of people sharing one and the same characteristic, for example one and the same sex or one and the same age bracket;
- the tone chart comprises orthosis colours, preferably consists of orthosis colours;
- in step 1), use is made of an acquisition apparatus chosen from among a mobile telephone and a tablet;
- in step 1), use is made of an acquisition apparatus comprising a screen displaying at least one reference marker to be associated with a reference of the calibration map so as to attain a predetermined acquisition position;
- in step 1), use is made of a calibration map configured to hug the shape of the limb and/or made of a hypoallergenic material and/or comprising an opening through which the skin of the limb is visible in the acquisition position;
- in step 2), use is made of a computer integrated into the apparatus used to acquire the photograph in step 1) or a computer independent of the said apparatus to which the said apparatus transfers the photograph on completion of step 1);
- at the end of step 2), an operator examines the orthosis colour determined by the computer and chooses to go to step 3) or to return to step 2) in order for the computer to select another orthosis colour, according to predefined criteria;
- before step 3), an operator chooses a range of orthoses from which the selection in step 3) is performed;
- preferably, before step 2), the operator chooses a range of orthoses from which the selection in step 3) is performed, and, in step 2), the computer selects the orthosis colour solely from among the orthosis colours which are colours of orthoses of the said range;

in step 3), the said selection is performed by computer and communicated to an operator of the computer;

the computer provides, preferably on a screen, a state of the stocks for the selected orthosis and/or provides a delivery timescale for the selected orthosis and/or is configured so that the operator can place an order for the selected orthosis.

Definitions

Any conventional calculation means is called a "computer". The computer can be integrated into the apparatus for acquiring the photograph, for example into a stills camera, a tablet or a mobile telephone. It can also be independent, and be for example a central computer or a personal computer (PC).

Unless indicated to the contrary, "comprising", "having", "including" or variations thereof are to be interpreted in a non-exclusive manner.

BRIEF DESCRIPTION OF THE DRAWINGS

Other characteristics and advantages of the invention will become further apparent on reading the detailed description which follows, and on examining the appended drawing in which FIG. 1 schematically represents an exemplary EVC orthosis.

DETAILED DESCRIPTION

Orthosis

Figure 1:
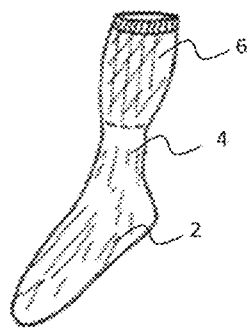

An orthosis, of tubular general shape, conventionally comprises a foot part 2 enveloping the foot and a leg part comprising an ankle part 4 enveloping the ankle and a calf part 6 enveloping the calf (FIG. 1).

The orthosis extends up to a level situated below the knee in the case where the orthosis is a "below-the-knee" sock (or "calf sock").

The configuration in sock form is not limiting, and the orthosis can also be produced in the form of "thigh highs", made longer by a compressive thigh part. The orthosis can also be produced in the form of tights, and/or be devoid of any foot part (stockings or tights of "open foot" type).

The pressure profile exerted by an orthosis is customarily degressive upwards starting from the ankle.

The orthoses are distributed according to the ASQUAL brand in four textile classes, from class I (13 to 20 hPa≈10 to 15 mmHg at the ankle) to class IV (>48 hPa≈>36 mmHg at the ankle).

To allow a compression of the lower limbs to a high pressure level achieving a therapeutic effect, an orthosis is conventionally produced from a knitted mesh and incorporates, in the leg part, an elastic weft yarn, generally of a lapped elastane.

This weft yarn, hardly visible when the orthosis is unstretched, in the "flat position", may become visible in the slipped-on position, thereby modifying the appearance of the orthosis.

The shade of the orthosis may therefore differ between the flat position and the slipped-on position.

Calibration Map

The calibration map 10 is intended in particular to serve as colorimetric reference for the analysis of the colours of photographs taken with the acquisition apparatus.

Figure 2:
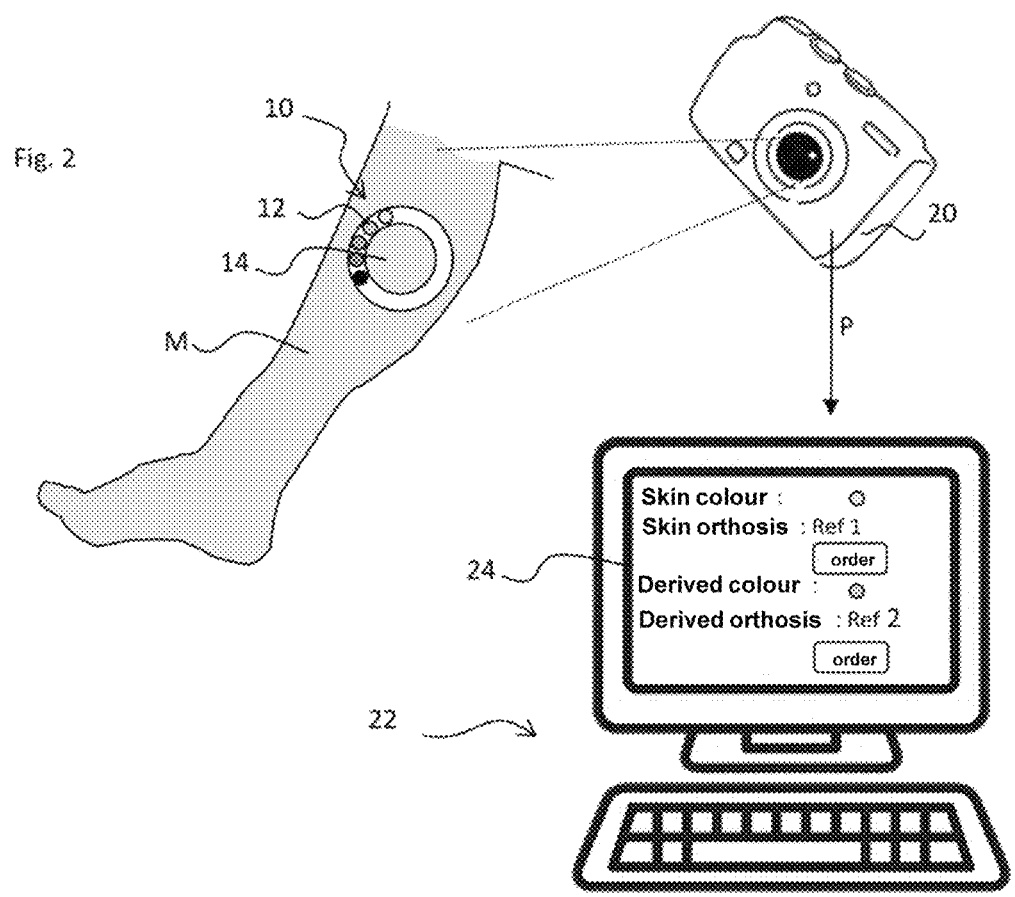
FIG. 2 schematically illustrates a method according to the invention, the calibration map being in the acquisition position.

The calibration map 10 is conventionally substantially plane. Preferably, it is flexible or semi-rigid, preferably so as to be able to hug the shape of the lower limb M on which it is applied (FIG. 2). It may for example be made of cardboard or plastic. Preferably, it is made of a hypoallergenic material.

By definition, a calibration map bears a plurality of calibration zones 12. Each calibration zone has a standardized colour which is known to the computer which, in step 2), performs the calibration. The colour is termed "standardized" when it has been determined under predetermined lighting conditions of the calibration zone.

In one embodiment, the calibration zones comprise patches of various colours, preferably skin colours of human beings. Preferably, the calibration map comprises more than 5, preferably more than 10 calibration zones each having a specific beige colour and liable to be the colour of a skin of a human being. In one embodiment, these beige colour zones represent more than 50%, more than 80%, preferably 100% of the calibration zones of the calibration map.

The calibration map preferably exhibits a thickness of less than 3 mm, preferably less than 2 mm, preferably less than 1 mm. Advantageously, in the acquisition position, the skin and the calibration zones 12 are substantially in the same plane. The precision of the colour evaluation is thereby improved.

Preferably still, the calibration zones 12 are disposed on the calibration map so as to be a distance, in the plane of the photograph, of less than 30 mm, preferably of less than 20 mm, preferably of less than 10 mm away from the skin. The calibration, on the basis of the calibration zones, advantageously makes it possible to culminate in a calibrated colour which is very close to the actual colour of the skin.

Preferably, the calibration map comprises an opening 14 through which the skin of the lower limb M can be visible in the acquisition position. The presence of an opening facilitates the analysis of the photograph, the computer used in step 2) preferably having means for identifying this opening on the photograph.

The shape of the opening is not limiting. It may emerge on the periphery of the calibration map, as a notch, or, preferably, be delimited by a closed outline. Preferably, it exhibits the shape of a disc, the calibration map being able in particular to take the form of an annulus, the calibration zones preferably being disposed around the opening.

Acquisition Apparatus

The acquisition apparatus 20 can be a stills camera or a video camera, preferably a stills camera or a video camera of a mobile telephone. It preferably comprises a computer adapted to perform the operations of steps 2) and, preferably, 3).

In one embodiment, the acquisition apparatus 20 has communication means, for example Bluetooth®, to communicate with a non-integrated computer 22.

Preferably, the acquisition apparatus comprises guidance means, preferably vocal or visual, to guide the operator when taking the photograph.

In particular, it can comprise a screen displaying at least one reference marker to be matched up with a corresponding reference of the calibration map. The guidance facilitates the positioning, by the operator, of the acquisition apparatus with respect to the calibration map.

For example, the screen can display a line (reference marker) corresponding to the outline of the opening (reference). By overlaying this line with the opening displayed on the screen, the operator is thus assured that the position of the acquisition apparatus is suitable for the implementation of the method. The reference markers can take any form, for example consist of a point, of a line or of any geometric shape, for example of two lines forming an angle or of an arrow. The references can in particular follow the outline of the calibration map or of the opening.

The screen can also display guidance messages, for example "get closer" or "modify the orientation of the apparatus". These may be audible messages.

Method

In step 1), an operator, for example the patient or the pharmacist, applies the calibration map 10 flat on the skin of the patient's lower limb. He keeps the calibration map in this position, termed the "acquisition position" (FIG. 2).

The patient's skin is then visible through the opening 14.

The operator then takes a photograph P representing the calibration map, with the photographic apparatus 22, preferably with his mobile telephone.

In step 2), the photograph is transmitted to the computer 22, integrated or otherwise into the photographic apparatus. The computer 22 may for example be a personal computer nearby, with which the photographic apparatus communicates, preferably by Bluetooth®.

The computer analyses the photograph P to identify the calibration zones 12 of the calibration map and the zone of the patient's skin that extends across the opening 14 of the calibration map 10. Any known means of image analysis can be envisaged. These means can be automatic, that is to say not require human intervention, or require the assistance of the operator. Preferably, they are automatic.

The company X-Rite markets the Color-Eye® device in particular.

The computer has in memory the information relating to the various calibration zones, for example the values of $L^*$, $a^*$ and $b^*$ in the 1976 CIE $L^*a^*b^*$ colour space, generally named CIELAB, for example in standardized daylight D65.

Having recognized the calibration zones, the computer can, for each calibration zone, compare its values of $L^*$, $a^*$ and $b^*$ on the photograph, or "apparent colorimetric values" with the values of $L^*$, $a^*$ and $b^*$ recorded in memory in the computer, or "actual colorimetric values". The computer then calibrates the photograph as a function of the differences between the apparent colorimetric values and the actual colorimetric values.

The photograph can be for example filtered so that on average, over the whole set of calibration zones, the disparity between the apparent colorimetric values and the actual colorimetric values is minimal.

The calibration of photographs is a conventional operation and any known scheme can be envisaged.

Calibration of the photograph leads to correcting the colour of the skin visible in the opening, until a colour substantially identical to the actual colour of the skin is obtained. The computer then determines this colour, termed the "calibrated colour" of the skin, or "complexion".

The calibration map therefore serves as colorimetric reference in order to calibrate the colours of the photograph according to the luminous environment when taking the photograph.

Moreover, the computer has, in its memory, a tone chart. A tone chart is a set of "tone chart colours" defined precisely in the colorimetric space used to calibrate the photograph.

Preferably, the tone chart comprises more than 5, more than 10, or more than 50 different tone chart colours, or indeed more than 100 different colours.

Preferably, the computer identifies a tone chart colour which exhibits the colour closest to that of the skin, that is to say to the calibrated colour.

The computer has access to a database providing, for each tone chart colour, an orthosis colour, preferably substantially identical to the tone chart colour, and the references of one or more orthoses which exhibit the said orthosis colour. For each tone chart colour selected, it can thus determine an orthosis colour and one or more orthoses of this colour.

Preferably, at least some, preferably each tone chart colour represents the colour of a respective orthosis, preferably measured in a flat position of the orthosis. The determination of the orthosis colour is therefore merged with the selection of the tone chart colour.

Preferably, the tone chart comprises a tone chart colour for each of the colours available for an orthosis model, preferably for several orthosis models, preferably for the whole set of available orthosis models.

Preferably, the computer presents, for example on a screen 24, the calibrated colour ("skin colour" in FIG. 2) and/or the references of one or more corresponding orthoses. Preferably, the computer preselects these references as a function of the treatment to be applied to the patient.

In one embodiment, the operator informs the computer, before step 2), of a range of orthoses which is suitable for the patient, for example by inputting the treatment to be applied. In step 2), the computer then selects, preferably, the tone chart colour solely from among the colours of the tone chart which are colours of orthoses of the said range or which are associated with colours of orthoses of the said range.

In step 3), the operator can thereafter choose an orthosis which exhibits a selected reference, preferably by means of the computer 22, and order it. Preferably, the computer has access to the stocks and to the delivery timescales and can indicate to the operator the timescale before he receives the orthosis.

The patient thereafter receives an orthosis which exhibits substantially the same colour as the skin of his lower limb.

Surprisingly, a study carried out among patients has however shown that this colour is not necessarily the one that is preferred by the patient. Statistically, for example on average over a group of patients, the patients often prefer another colour.

With each tone chart colour, a preferred colour, termed the "derived colour", has been identified. A database can provide, for each tone chart colour, a derived colour which is different from the orthosis colour closest to the calibrated colour.

In one embodiment, the derived colour can be determined for a group of patients exhibiting at least one common character. Preferably, the derived colour is the preferred colour for a sample of patients for whom the analysis of a photograph of one of their lower limbs, with the calibration map 10, has led to the said calibrated colour. The group can be a group of patients belonging to one and the same age class and/or having a similar social profile, for example sharing the same socio-professional class and/or of the same sex.

In a preferred embodiment, the computer presents, alternatively or in addition to the calibrated colour, the derived colour and/or the reference of an orthosis exhibiting this derived colour. Preferably, it further allows the operator to know the stocks and/or to know the delivery timescale and/or to place an order.

As is now clearly apparent, the invention makes it possible to rapidly and reliably determine one or more orthosis references liable to please the patient. The patient can therefore proceed in an enlightened manner with the choice of the orthosis that he has to wear. This results in better observance.

In particular, the invention makes it possible to determine a so-called "bare skin" effect of the colourway. By allowing the choice of the more "aesthetic" orthoses, it thus responds to patients' expectations and therefore improves their degree of satisfaction.

Of course, the invention is not limited to the embodiments described and represented, provided for illustration purposes only.

The invention claimed is:

1. Method for selecting an elastic venous restraint orthosis intended to be slipped onto a lower limb of a patient, the said method comprising the following steps:
   1) acquisition of a photograph representing the skin of the said limb and a calibration map comprising one or more calibration zones, the calibration map being placed on the said limb in a position termed the "acquisition position";
   2) calibration of the photograph by means of the calibration zone or zones, in such a way that the representation of the said skin on the photograph exhibits a calibrated colour, and then selection, as a function of the calibrated colour, by computer and from a set of colours of a tone chart, of a tone chart colour, termed the "optimal colour", and then determination, by computer, of an orthosis colour as a function of the tone chart colour selected;
   3) selection of an orthosis exhibiting the said orthosis colour.

2. Method according to claim 1, in which, in step 2), the orthosis colour determined in step 2), termed the "derived colour", is different from the orthosis colour closest to the tone chart colour selected.

3. Method according to claim 2, in which the derived colour is determined by statistical analysis of responses of a group of patients to an opinion survey.

4. Method according to claim 3, in which the group of patients consists of people for whom the implementation of steps 1) and 2) culminates in the said selected tone chart colour.

5. Method according to claim 3, in which the group of patients consists of people sharing one and the same characteristic.

6. Method according to claim 1, in which the tone chart comprises orthosis colours.

7. Method according to claim 1, in which, before step 2), the operator chooses a range of orthoses from which the selection in step 3) is performed, and, in step 2), the computer selects the orthosis colour solely from among the orthosis colours which are colours of orthoses of the said range.

8. Method according to claim 1, in which, in step 1), use is made of an acquisition apparatus chosen from among a mobile telephone and a tablet, the said acquisition apparatus comprising a screen displaying at least one reference marker to be associated with a reference of the calibration map so as to attain a predetermined acquisition position.

9. Method according to claim 1, in which, in step 1), use is made of a calibration map configured to hug the shape of the limb in the acquisition position or made of a hypoallergenic material or comprising an opening through which the skin of the limb is visible in the acquisition position.

10. Method according to claim 1, in which, in step 2), use is made of a computer integrated into the apparatus used to acquire the photograph in step 1) or a computer independent of the said apparatus to which the said apparatus transfers the photograph on completion of step 1).

11. Method according to claim 1, in which, in step 3), the said selection is performed by computer and communicated to an operator of the computer.

12. Method according to claim 11, in which the computer provides a state of the stocks of the selected orthosis or a delivery timescale for the selected orthosis or is configured so that the operator places an order for the selected orthosis.

* * * * *